United States Patent [19]

Piechota, Jr.

[11] Patent Number: 5,256,396
[45] Date of Patent: Oct. 26, 1993

[54] TOPICAL COMPOSITION

[75] Inventor: Stanley E. Piechota, Jr., Somerset, N.J.

[73] Assignee: Colgate-Palmolive Company, Piscataway, N.J.

[21] Appl. No.: 469,198

[22] Filed: Jan. 24, 1990

[51] Int. Cl.$^5$ .......... A61K 7/16; A61K 7/18; A61K 7/22

[52] U.S. Cl. .......... 424/49; 424/52; 424/54

[58] Field of Search .......... 424/49–58; 514/944

[56] References Cited

U.S. PATENT DOCUMENTS

| | | | |
|---|---|---|---|
| 2,773,801 | 12/1956 | Fox | 424/49 |
| 2,921,885 | 1/1960 | Bouchal | 167/93 |
| 3,001,944 | 9/1961 | Ywei | 252/117 |
| 3,639,563 | 2/1972 | Januszewski | 424/49 |
| 3,766,097 | 10/1973 | Rosmarin | 252/552 |
| 3,976,765 | 8/1976 | Nachtigal | 424/54 |
| 4,011,309 | 3/1977 | Lutz | 424/49 |
| 4,206,198 | 6/1980 | Schmolka | 424/49 |
| 4,323,582 | 4/1982 | Schmolka | 424/54 |
| 4,411,889 | 10/1983 | Kaslavsky | 424/151 |
| 4,431,631 | 2/1984 | Clipper et al. | 424/53 |
| 4,465,661 | 8/1984 | Schmolka | 424/58 |
| 4,537,778 | 8/1985 | Clipper et al. | 424/53 |
| 4,678,664 | 7/1987 | Schmolka | 424/65 |
| 4,684,517 | 8/1987 | Clipper et al. | 424/52 |
| 4,696,757 | 9/1987 | Blanic | 424/53 |
| 4,759,925 | 7/1988 | Gaffar et al. | 424/52 |
| 4,784,788 | 11/1988 | Lancz | 252/114 |
| 4,839,156 | 6/1989 | Ng et al. | 424/53 |
| 4,843,099 | 6/1989 | Gaffar | 514/576 |

OTHER PUBLICATIONS

Schmolka, Cosmetics & Perfumery, Apr. (1974), 63.
Pader, Surfactants in Cosmetics, Surfactant Science series, (1985), pp. 306–307.
BASF Brochure Pluronic & Tetronic Surfactants, (1987), p. 17.

Primary Examiner—Shep H. Rose
Attorney, Agent, or Firm—Paul Shapiro; Robert C. Sullivan

[57] ABSTRACT

In accordance with the teachings of this invention, a composition and method for the topical application of a water dispersible active ingredient to a surface of a warm blooded animal is provided. Specifically, such composition is provided to have the properties of being readily flowable upon filling a container therewith, maintaining such flowable condition after storage for a substantial length of time and being readily flowable upon application to the desired animal situs. Uniquely, upon contact with the warm surface of the animal then, and only then, does the composition quickly forms into a non-flowable relatively substantive gel. Specifically such composition comprises:

(a) a water soluble non-ionic block copolymer of ethylene oxide and propylene oxide of the formula $HO(C_2H_4O)_a(C_3H_6O)_b(C_2G_4O)_cH$;

(b) the active ingredient to be topically delivered; and (c) water.

7 Claims, No Drawings

TOPICAL COMPOSITION

BACKGROUND OF THE INVENTION

This invention relates generally to the provision of compositions for the topical application of a water soluble active ingredient to a surface of a warm blooded animal including humans. In particular, this invention relates to such a composition which can be applied as a relatively low viscosity flowable liquid and which will quickly, upon contact with the warm surface of such animal, turn into a relatively high viscosity, essentially non-flowable, gel.

The field of applying active ingredients topically to humans and animals is, of course, wide ranging and comprises for example, the application of active ingredient for therapeutic, prophylactic and cosmetic purposes. Notwithstanding this wide and varying range of purposes, a great many of such applications suffer from a common problem. Specifically, it is desirable to provide such compositions in a pourable, flowable liquid form so that containers for the composition can easily be filled, the composition can easily be dispensed from such containers and the composition can easily be applied to the desired situs; either by mechanical means e.g., a syringe and needle, a spray or pump, or by hand. On the other hand, once the composition has been packaged, dispensed and applied to the situs, it is desirable that the composition no longer flow but instead remain in place and release the active ingredient.

As an example, it is desirable to topically apply certain therapeutic liquids into subgingival pockets in the treatment of periodontal disease. Injection devices employed for the purpose utilize fitments with small orifices to enable the injection tip to fit into the subgingival pocket easily without inflicting excessive pain to a patient. An example of such a device is described in U.S. Pat. No. 4,617,918. Clearly, to flow through the small orifices of such devices, the composition must be of relatively low viscosity and easily flowable. Once delivered to the subgingival pockets, however, it is desirable that the composition remain in place and deliver the medicament to the affected tissue. A low viscosity fluid will obviously not suffice for this purpose.

The problem of providing a composition having these apparently contradictory properties (i.e., flowable during filling, dispensing and applying while non-flowable after being applied to the desired situs) has been addressed in U.S. Pat. No. 4,411,889 to Caslavsky, et al. This specification teaches the provision of a composition for topical delivery of fluoride or antibacterial agents to the oral cavity and employs a composition said to be a low-viscosity, aqueous solution adapted to be converted, after mixing and topical application, from a liquid solution to a gel state. The operative ingredients in this invention comprise a silica acid ester monomer or prepolymer which on hydrolysis forms silica polymer when in the presence of one or more gelling agents such as gel catalysts or silicate esters. The gelling is initiated and it is taught that from anywhere from 24 hours to less than one minute after combining the gelling agent with the remainder of the composition, gelling is effected. Thus while the composition accomplishes the result of in situ gelling after application, in practice, several drawbacks are manifested. In use, it is incumbent upon the applier to first mix the composition with the gelling agent and hence requires weighing and/or measuring and mixing; operations which are clearly inconvenient to a professional and totally impractical to a lay consumer. Moreover, there is an exquisite timing requirement in using such compositions: the mixing must occur closely enough to application so as to provide sufficient working time prior to gelling and yet upon application the composition must gel quickly enough to realize the benefits of an applied gel. Such precise timing once again represent great inconvenience for the professional and essentially precludes use by the lay user.

Accordingly, there is a need for a composition which can be filled and stored, as a flowable liquid, dispensed as a liquid and, without the need for any further mixing or measuring, applied to a desired situs where it will quickly form, in situ, into a gel.

SUMMARY OF THE INVENTION

In accordance with the teachings of this invention, an oral composition and method for the topical application of a water dispersible active ingredient to a surface of a warm blooded animal is provided. Specifically, such composition is provided to have the properties of being readily flowable upon filling a container therewith, maintaining such flowable condition after storage for a substantial length of time and being readily flowable upon application to the desired animal situs. Uniquely, upon contact with the warm surface of the animal then, and only then, does the composition quickly forms into a non-flowable relatively substantive gel. Specifically such composition comprises:
  (a) a water soluble non-ionic block copolymer of ethylene oxide and propylene oxide of the formula

(b) the active ingredient to be topically delivered; and
  (c) water.

The block copolymer is preferably chosen (with respect to a, b, and c) such that the ethylene oxide constituent comprise from about 65 to about 75%, by weight, of said copolymer molecule and the copolymer has an average molecular weight of from about 11,000 to about 13,000 and with said copolymer being provided in such quantity that the composition is flowable at temperatures below 80° F. (26.7° C.) and forms a gel upon contact with the surface of such warm blooded animal. Preferably, the weight percent of the copolymer in the composition should be greater than ten percent and not less than twenty percent and still more preferably from about twelve to about seventeen percent.

The above described composition will maintain a low viscosity and be relatively flowable at temperatures below about 80° F. (26.7° C.). Upon contact with the surface of a warm animal having a body temperature above 80° F. (26.7° C.) e.g., 98° to 99° F. (36.7°-37.2° C.), as in a human, the composition will gel within seconds and cease to flow without the application of substantial force.

The invention finds particular use as a liquid dispersion for the topical application of active ingredients to the oral cavity. Further, in another aspect of the invention the composition may be employed to facilitate the application of an active ingredient to a warm surface, e.g. when the active ingredient to be applied by first dispensing the composition onto the applier's hand. In accordance with the teachings herein, such composition will be dispensable onto the warm surface as a flowable liquid and then gel so as to preclude undesirable dripping from such surface. Thus for example the composition may be dispensed onto an applier's hand where it will gel and facilitate further application.

The ethylene oxide/propylene oxide block copolymer of the composition of the invention is selected from a group of water soluble polyalkylene glycol block copolymers known generically as poloxamers.

In accordance with the teachings of this invention the poloxamer chosen is one in which the ethylene oxide units constitute from about 65 to about 75%, by weight of said copolymer molecule. The copolymer has an average molecular weight of from about 11,000 to 13,000 and preferably from about 12,000 to about 13,000. The poloxamer of choice is designated poloxomer 407 and has an average molecular weight of about 12,500. The poly(ethylene oxide) blocks average 67 moles, i.e. about 60%, by weight. Poloxamer 407 as described by the manufacturer is nontoxic, exhibiting in rat studies an $LD_{50}$ of 15.4 g/kg and in studies with rabbits, an acute dermal toxicity greater than 2 g/kg. An aqueous solution of 20% by weight of Poloxamer 407 was found by the manufacturer to be non-irritating in a Draize Rabbit Eye irritation study. Table 1 set out some of the physical properties of this preferred poloxamer 407 as sold by the BASF Wyandotte Corporation of Parsippany N.J. under the trademark PLURONIC F127.

TABLE 1

| Physical Properties of Poloxamer 407 | |
| --- | --- |
| Average molecular weight | 12,600 |
| Melt Point | 56° C. |
| Physical Form at 20° C. | Solid |
| Brookfield Viscosity at 77° C. | 3100 cps. |
| Surface tension at 25° C., 0.1% | 41 dynes/cm. |
| Draves Wetting at 25° C. | |
| 1.0% | >360 |
| 0.1% | >360 |
| Foam Height | 40 mm |
| (Ross Miles 0.1%, aqueous at 50° C.) | |
| Cloud Point in aqueous Solution | |
| 1.0% | >100° C. |
| 10% | >100° C. |
| HLB (hydrophilic lipophilic balance) | 18-23 |

Poloxomer 407 is virtually tasteless and odorless and hence has found use in solubilization of aromatics in oral hygiene products such as aqueous alcoholic mouthwashes. As usual in these compositions, the concentration is quite low (less than 10% by weight and generally less than 1% by weight) and hence such compositions do not exhibit the self gelling properties described herein. The poloxamer compounds are indeed known to be useful in forming gels and, in fact are so described in a brochure of the aforementioned BASF Corporation entitled Pluronic & Tetronic Block Copolymers Surfactant pp. 16-17 (1987). In a further publication of BASF entitled Technical Data of Pluronic Polyols, the recommended procedure is described for forming gels from Pluronic F127 solutions. It is said that gels will be formed with concentrations having a minimum of 20% by weight of such compound and may be formed by dissolving the Pluronic F127 at 80° C. into the solution and cooling to room temperatures to form the gel. Alternatively, the Pluronic ® F127 may be dissolved into a water solution at 5° to 10° C. and then brought to room temperature whereupon it forms a ringing gel. As is apparent, these teachings would not lead one skilled in the art to employ Pluronic F127 to meet the objects of this invention in that such teachings are totally inimical to the objects of this invention; it is taught that the result is a gelled solution at room temperature i.e., one that cannot be filled, stored or dispensed as a flowable liquid.

Instead, it has now been discovered that by employing poloxamer 407, in concentrations untaught by the prior art namely, greater than ten percent and less than twenty percent and preferably from twelve to seventeen percent) an aqueous single phase solution is produced which is liquid and flowable at room temperature and will gel in only a few seconds when elevated to about 80° F. Specifically, it has been discovered that such a composition having such properties will result if the poloxamer is poloxamer 407 and is employed in concentrations heretofore untaught by the prior art namely, of greater than ten percent and less than twenty percent. Preferably such concentration should range from about twelve to about seventeen percent. While the mechanism for the phenomenon of gelling at the desired temperature is not completely clear, it is believed that such behavior is totally dependent on the choice of a specific narrow range of defining parameters for the polymer e.g., molecular weight and proportions of ethylene oxide to propylene oxide units together with the choice of a narrow band of concentrations of the polymer in the composition.

The teachings of this invention are broadly applicable to a large number of aqueous compositions intended to deliver active ingredients to the situs of a warm animal. Such compositions may include therapeutic compositions wherein the active ingredient is a medicament as, for example, the topical delivery of resorcinol for treating various dermatological conditions, the delivery of adrenocorticoids as an antiinflammatory or the use of retinoids in acne treatment. A specific example of this is described in U.S. Pat. No. 4,843,009 wherein Ibuprofen is delivered to the oral cavity. The composition may be employed to deliver active ingredients for prophylactic purposes e.g. an antiseptic or antimicrobial agent. The invention is equally applicable for delivery active ingredients for cosmetic purposes e.g. as a cooling lotion or astringent or for delivery of perfumes or deodorants.

A particularly useful employment of the teachings of this invention is a liquid dispersion e.g., a mouthwash, for delivering prophylactive or therapeutic active ingredients to the oral cavity. Such active ingredients may include antimicrobial and antibiotic agents e.g. triclosan, chlorhexidene, alexidine, cetylpyridinium chloride or sanguinarine as well as essential oils, fluorides providing anticaries properties, astringents such as zinc compounds. Some typical anti-microbial agents are set out with greater particularity in commonly assigned copending British patent application 8801773, published as GB 2200551A on Aug. 10, 1988. Such active ingredients may also include astringent salts which form a thin protective film on the surface of body cells and hence lessen the cells sensitivity to external stimuli such as might be caused by mechanical, thermal or chemical action. Examples of astringent compounds utilized in orally applied compositions include zinc salts such as zinc chloride and zinc citrate which are soluble in water. Such active ingredient may also include certain compounds for the purpose of topical deodorization such as, for example, chlorophyllins. Additionally, such active ingredient may include fluorides as anticaries agents such as sodium fluoride, stannous fluoride, sodium monofluorophosphate, and the like. It will be understood that the above recitation of active ingredients is merely exemplary and that many others will occur to one skilled in the art as usable within the teachings of this invention.

In addition to such active ingredients, additional components are typically employed in oral aqueous compositions including such additional components as alcohol, flavor, humectants and surfactants.

Alcohols are employed, in denatured form, in concentrations of about 5 to about 30% for the various purposes of enhancing the impact of a flavor ingredient, enhancing antimicrobial efficacy or for facilitating the solubility of other ingredients. Suitable alcohols are for example ethanol or isopropenol.

Flavors utilized in mouth washes for example, include such ingredients as eucalyptol, menthol, thymol, methyl salicylate together with flavor modifies. Additionally, certain mint-type flavors and cinnamon type flavors have been employed including for example peppermint, spearmint or clove. Frequently, sweeteners such as saccharin compounds are also included.

Humectants are employed primarily to prevent crystallization around closures. Glycerin sorbitol, polyethylene glycol, and polypropylene glycol being generally the humectants of choice.

Additionally, as has been described above, surfactants have been employed, primarily to aid in the solubilization of some of the other ingredients and to provide a foaming action if desired. In addition to the poloxamer compounds described above, such surfactants may include other non-ionics such as polyethylene fatty acid esters, and sorbitan monostearate as well as cationics such as cetylpyridinium chloride or anionics such as sodium lauryl sulfate.

The invention may also be employed in a cosmetic preparation such as an after shave lotion where the active ingredient is essentially a denatured alcohol. Other ingredients in such a composition may include perfumes and coloring agents.

DESCRIPTION OF CERTAIN EMBODIMENTS

The following examples are further illustrative of the nature of the present invention. All amounts and properties referred to herein are by weight.

EXAMPLE 1

An antimicrobial mouthrinse is prepared comprising chlorhexidine digluconate as the active antimicrobial agent.

| Ingredient | Weight Percent |
| --- | --- |
| Deionized Water | 78.98 |
| Ethanol (190°) | 5.00 |
| Sodium Saccharin | 0.20 |
| Hibitane (20% Chlorhexidine digulconate) | 0.12 |
| Pluronic F-127 | 15.00 |
| Flavor 89-180 | 0.10 |
| FD&C Blue #1 (0.1% Sol.) | 0.30 |
| FD&C Yellow #5 (0.1% Sol.) | 0.30 |
| | 100.00 |

This composition is a flowable liquid at temperatures below 82° F. (27.8° C.), and when heated to 82° F. the composition gels in less than one minute. The sample gels upon contact with the oral surface.

EXAMPLE 2

An antimicrobial mouthrinse is prepared comprising cetylpyridinium chloride as the active antimicrobial agent.

| Ingredient | Weight Percent |
| --- | --- |
| Deionized Water | 79.00 |
| Sodium Saccharin | 0.20 |
| Ethanol (190°) | 5.00 |
| Getylpyridinium Chloride | 0.10 |
| Pluronic F-127 | 15.00 |
| Flavor 89-180 | 0.10 |
| FD&C Blue #1 (0.1% Sol.) | 0.30 |
| FD&C Yellow #5 (0.1% Sol.) | 0.30 |
| | 100.00 |

Again, this composition is a flowable liquid below 82° F. and when heated to 82° F. (27.6° C.), gels in less than one minute. The sample gels upon contact with the oral surface. Accordingly, the use of alternative antimicrobial agents does not effect the desired gelling phenomenon.

What is claimed is:

1. An oral composition for the topical application of a water dispersible active ingredient to a surface of a warm blooded animal comprising:
   (a) a water soluble, nonionic block copolymer of ethyleneoxide and propylene oxide of the formula HO(C$_2$H$_4$O)a(C$_3$H$_6$O)b(C$_2$H$_4$O)cH, wherein the ethylene oxide units comprise from about 65 to about 75% by weight of said copolymer and said copolymer has an average molecular weight of from about 11,000 to about 13,000; the copolymer comprising more than 10 to about 17% by weight of said composition;
   (b) said active ingredient; and
   (c) water; said composition being flowable at temperatures below 80° F. and forms a gel upon contact with said oral surface of said warm blooded animal.

2. The composition of claim 1 wherein said copolymer has an average molecular weight of from about 12,000 to about 13,000.

3. A liquid dispersion for the topical application of active ingredients to the oral cavity comprising:
   (a) a water soluble, nonionic block copolymer of ethylene oxide and propylene oxide of the formula HO(C$_2$H$_4$O)$_a$ (C$_3$H$_6$O)$_b$ (C$_2$H$_4$O)$_c$H, wherein the ethylene oxide units comprise from about 65 to about 75% by weight of said copolymer and said copolymer has an average molecular weight of from about 11,000 to about 13,000; the copolymer comprising from more than 10 to less than 17% by weight of the composition;
   (b) said active ingredient, selected from one or more of the group consisting of antimicrobial agents, anticaries fluorides, astringents, and topical deodorizers; and
   (c) water; said composition being flowable at temperatures below 80° F. and forms a gel upon contact with warm surfaces of the oral cavity.

4. The composition of claim 3 wherein said copolymer has an average molecular weight of from about 12,000 to about 13,000.

5. A method for the facile application of an active ingredient to the oral cavity comprising:
   (a) maintaining an aqueous dispersion of said active ingredient at a temperature below 80°F., said aqueous dispersion comprising a water soluble, non-ionic, block copolymer of ethylene oxide and propylene oxide of the formula HO $(C_2H_4O)_a (C_3H_6O)_b (C_2H_4O)_c$ H wherein the ethylene oxide units comprise from about 65 to about 75% by weight of said copolymer and said copolymer has an average molecular weight of from about 11,000 to about 13,000; the copolymer comprising from more than 10 to about 17% by weight of the composition, the composition being flowable at temperatures below 80° F. and forms a gel at temperatures above 80°F.; and (b) applying said aqueous dispersion to the oral cavity to form such gel.

6. The method of claim 5 wherein said copolymer has an average molecular weight of from about 12,000 to about 13,000.

7. The method of claim 5 wherein the active ingredients are selected from one or more of the group consisting of antimicrobial agents, anticaries fluorides, astringents and topical deodorizers.

* * * * *